(12) United States Patent
Craig et al.

(10) Patent No.: US 8,642,665 B2
(45) Date of Patent: Feb. 4, 2014

(54) ENVIRONMENTALLY FRIENDLY, LOW WHITENING COMPOSITIONS

(71) Applicant: Conopco, Inc., d/b/a Unilever, Englewood Cliffs, NJ (US)

(72) Inventors: Jennifer Lyn Craig, Trumbull, CT (US); Vivek Subramanian, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/679,220

(22) Filed: Nov. 16, 2012

(65) Prior Publication Data

US 2013/0156709 A1    Jun. 20, 2013

Related U.S. Application Data

(60) Provisional application No. 61/576,578, filed on Dec. 16, 2011.

(51) Int. Cl.
*A01N 31/08* (2006.01)

(52) U.S. Cl.
USPC ............................................. 514/731; 424/401

(58) Field of Classification Search
None
See application file for complete search history.

(56) References Cited

U.S. PATENT DOCUMENTS

| | | | |
|---|---|---|---|
| 5,833,973 A | 11/1998 | Dobkowski et al. | |
| 6,007,801 A | 12/1999 | Hossel et al. | |
| 6,074,672 A | 6/2000 | Dobkowski et al. | |
| 6,146,616 A | 11/2000 | Msika et al. | |
| 6,495,122 B2 | 12/2002 | Fankhauser et al. | |
| 2002/0131785 A1 | 9/2002 | Ito | |
| 2007/0054967 A1* | 3/2007 | Schmaus et al. | 514/717 |
| 2010/0068162 A1 | 3/2010 | Greenberg et al. | |
| 2012/0308492 A1 | 12/2012 | Allef et al. | |

FOREIGN PATENT DOCUMENTS

| | | |
|---|---|---|
| EP | 0834300 | 4/1998 |
| EP | 1068866 | 1/2001 |
| EP | 1595527 | 11/2005 |
| FR | 2914859 | 10/2008 |
| WO | 2007048522 | 5/2007 |
| WO | 2011012395 | 2/2011 |

OTHER PUBLICATIONS

Makari, Retrieved online [Mar. 2, 2013], Retrieved from URL:<http://web.archive.org/web/20100619230238/http://www.makari.com/Makari-Ingredients.html>, Jun. 2010.*
PCT International Search Report and Written Opinion on International Application No. PCT/EP2012/074905 dated Mar. 22, 2013.

* cited by examiner

*Primary Examiner* — Lezah W Roberts
*Assistant Examiner* — Nannette Holloman
(74) *Attorney, Agent, or Firm* — Edward A. Squillante, Jr.

(57) ABSTRACT

Environmentally friendly, low whitening compositions are described. The compositions have aromatic alcohols and esters with a melting point from about 20° C. to about 40° C. The compositions are substantially free of silicones and suitable to impart excellent sensory characteristics in the absence of whitening and when topically applied to the skin of a consumer.

9 Claims, No Drawings

ENVIRONMENTALLY FRIENDLY, LOW WHITENING COMPOSITIONS

FIELD OF THE INVENTION

The present invention is directed to an environmentally friendly, low foam generating composition that comprises aromatic alcohols. More particularly, the present invention is directed to a low foam generating composition that comprises, in addition to an aromatic alcohol, an ester generally having a melting point from about 20° C. to about 40° C. The composition surprisingly yields excellent sensory benefits when topically applied, even when formulated substantially free of silicone. Such composition works well as a base that is silky upon application and capable of delivering active ingredients to skin.

BACKGROUND OF THE INVENTION

A variety of consumer-based compositions comprise silicones. Silicones are often desired because many are liquids at room temperature and they possess characteristics that make them excellent delivery vehicles or emollients of choice for many consumer products. Typically, silicones are employed as the emollient of choice in personal care products like face and body lotions, make-ups, deodorants, antiperspirants as well as hair care products. Their use is enjoyed by consumers because products with the same impart soft and silky feelings to the skin with little or no oily residue. Moreover, products with the same are easy to apply and free of foaming, even after applying with little shear.

Notwithstanding the positive benefits delivered with compositions having silicones, the use of silicones may raise safety and environmental concerns, and particularly, because silicones are resistant to biodegradation by microorganisms.

There are increasing interests to develop compositions that possess the characteristics of silicone comprising compositions but that are substantially free of silicones. This invention, therefore, is directed to an environmentally friendly, low foam generating composition comprising aromatic alcohols. The composition further comprises an ester having a melting point from about 20° C. to about 40° C. wherein the composition unexpectedly has excellent sensory benefits when applied and when formulated substantially free of silicone. Surprisingly, the composition works well as a base that is silky upon application and is capable of delivering active ingredients to skin. Furthermore, the composition of this invention is easy to apply and does not yield a white and foamy coating after applying with moderate and conventional shear. The composition of this invention yields a sensory-foam factor that is less than 25 gL* which indicates the same provides excellent sensory characteristics and low foaming or whitening after topical application.

ADDITIONAL INFORMATION

Efforts have been disclosed for making topical compositions. In U.S. Patent Application No. 2010/0068162 A9, compositions having carbon-based replacements for volatile silicones are described.

Still other efforts have been disclosed for making topical compositions. In U.S. Patent Application No. 2002/131785 A1, systems for customizing personal care products are described.

Even other efforts have been described for making topical compositions. In U.S. Pat. Nos. 6,074,672 and 5,833,973, powdered cosmetic compositions and compositions with cross-linked elastomeric silicones are described, respectively.

None of the additional information describes, as claimed in this invention, an environmentally friendly and low foam generating composition that provides silky attributes after being applied.

SUMMARY OF THE INVENTION

In a first aspect, the present invention is directed to a topical composition comprising:

a) an alcohol having the formula:

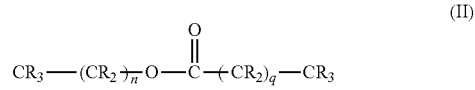

and b) an ester having the formula:

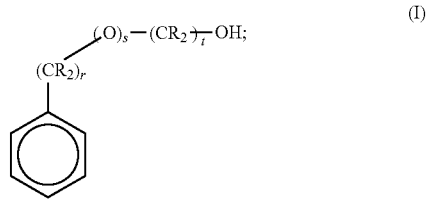

wherein each R is independently hydrogen or a methyl group;

r is 0 or 1, s is 0 or 1, t is an integer from 1 to about 6, n is an integer from about 5 to about 20 and q is an integer from about 3 to about 10.

In a second aspect, the present invention is directed to a method for imparting a silky feeling to skin by applying the composition of the first aspect of this invention.

All other aspects of the present invention will more readily become apparent upon considering the detailed description and examples which follow.

Topical composition, as used herein, is meant to include a composition suitable for application to skin of mammals, especially humans. Such a composition may be generally classified as leave-on or rinse-off, and is meant to include conditioners or tonics, lipsticks, color cosmetics, and general topical compositions that in some fashion improve a skin characteristic.

The topical composition of this invention can be in the form of, for example, a liquid, lotion, cream, serum, gel, soap bar, or toner, or applied via a face mask or patch.

Silky, as used herein, is meant to mean smooth and dry, having the feel of a composition with about 1-12% by weight silicone such as cyclomethicone and dimethicone cross-polymer as made available from suppliers like Dow Corning® as DC9040, 9045 and 9056 silicone elastomer blends. Substantially free of silicone means having less than 1%, and preferably, less than 0.5% silicone, and most preferably, from about 0.001% to about 0.3% by weight silicone. Optimally, the composition of this invention has 0.0% by weight silicone. Environmentally friendly, as used herein, means substantially free of silicone. Low foam generating as used herein means having non-visible aeration and after application. Low foam generating is also meant to mean essentially free of whitening after application with shear. Composition is broadly meant to include final composition wherein final composition, as used herein, means a composition comprising the aromatic alcohol and ester of this invention in final form for sale and application onto the skin of a consumer. Such a final form composition typically comprises an active suitable to benefit skin. Sensory-foam factor is the multiple of sensory assessment in grams and whitening or intensity (L*) utilizing standard L*, a*, b* analysis.

Comprising, as used herein, is meant to include consisting essentially of and consisting of. Therefore, it is within the scope of this invention for the composition to have an alcohol and ester mixture consisting essentially of or consisting of the alcohol and ester represented by formula I and II. All ranges identified herein are meant to implicitly include all ranges subsumed therein if, for example, reference to the same is not explicitly made.

The composition of this invention is one that at the very least, can be a base that carries active, for example, to lighten skin, moisturize skin, darken skin and/or reduce wrinkles on skin. Skin is meant to include skin on the face, neck, chest, back, arms (including underarms), hands, legs, buttocks and scalp.

DETAILED DESCRIPTION OF THE PREFERRED EMBODIMENTS

The only limitation with respect to the aromatic alcohol that may be used in the invention is that the same is represented by formula I and suitable for use in topical compositions.

Often, the preferred aromatic alcohol represented by formula I is one where s is zero, R is H and t is an integer from 1 to 3. In another preferred embodiment, the aromatic alcohol used in this invention is one where s is 1, R is H and t is 1 to 3. In a most preferred embodiment, the aromatic alcohol used in this invention is phenoxyethanol, benzyl alcohol or a mixture thereof.

Typically, the amount of alcohol used ranges from about 0.02 to about 6%, and preferably, from about 0.03 to about 4%, and most preferably, from about 1 to about 3% by weight, based on total weight of the composition and including all ranges subsumed therein.

The ester suitable for use and represented by formula II is limited only to the extent that the same may be used in a topical composition and has a melting point from about 20° C. to about 40° C., and preferably, from about 22° C. to about 38° C., and most preferably, from about 23° C. to about 36° C., including all ranges subsumed therein.

In a preferred embodiment, the ester is one where R is H, n is 12 to 19 (most preferably, 13 to 18) and q is 3 to 6 (most preferably, 4 to 6). In an especially preferred embodiment, the ester used in this invention is stearyl heptanoate, stearyl caprylate or a mixture thereof. The amount of ester typically used ranges from about 0.01 to about 30%, and preferably, from about 0.1 to about 15% and most preferably, from about 1 to about 8% by weight, based on total weight of the composition and including all ranges subsumed therein.

In an especially preferred embodiment at least 50%, and preferably, at least 75%, and most preferably, from about 80% to about 100% of all alcohol and ester used in the composition (including final composition) of this invention are represented by formulas I and II, respectively. The alcohol (formula I) and ester (formula II) are used herein to replace silicone in that they result in a composition with sensory characteristics typically observed when a composition that is not substantially free of silicone is made.

It should be known, nevertheless, that commercially acceptable and conventional vehicles may optionally be used, acting as diluents, dispersants and/or co-carriers along with the aromatic alcohols and esters described herein and any other optional but often preferred additives. Therefore, the overall/final composition comprising the alcohol and esters described herein may be aqueous-based, anhydrous or an emulsion including a water-in-oil or oil-in-water emulsions. If the use of water is desired, water typically makes up the balance of the final composition, and preferably, makes up from about 5 to about 95%, and most preferably, from about 40 to about 85% by weight of the topical composition, including all ranges subsumed therein.

In addition to water, organic solvents may be optionally included to act as carriers or to assist carriers within the compositions of the present invention. Illustrative and non-limiting examples of the types of organic solvents suitable for use in the present invention include aliphatic alkanols like ethyl or isopropyl alcohol, mixtures thereof or the like.

Other optional additives suitable for use include oils like avocado oil, almond oil, olive oil, neopentylglycol dicaprate, mixtures thereof or the like. Typically, such oils assist in emulsifying the final composition of this invention, and an effective amount may be used to yield a stable emulsion. In a preferred embodiment, the emulsions of this invention are oil-in-water emulsions.

Emollients may also be used, if desired, as co-carriers within the composition of the present invention. Alcohols, including alkadecanols, such as cetyl alcohol, are often desired as are the emollients generally classified as synthetic esters.

The ester emollients that may optionally be used are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, stearyl stearate and arachidyl behenate.
(5) Sterols esters, of which cholesterol fatty acid esters are examples.

Emollients when used, typically make up from about 0.1 to about 50% by weight of the composition, including all ranges subsumed therein.

Fatty acids having from 10 to 30 carbon atoms may also be included as cosmetically acceptable carriers within the composition of the present invention. Illustrative examples of such fatty acids include pelargonic, lauric, myristic, palmitic, stearic, isostearic, oleic, linoleic, arachidic, behenic or erucic acid, and mixtures thereof. Compounds that are believed to enhance skin penetration, like dimethyl sulfoxide, may also be used as an optional co-carrier. When used, from about 0.01 to about 5% by weight fatty acid is present in the composition.

Humectants of the polyhydric alcohol type may also be employed in the compositions of this invention. The humectant often aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.2 to 25%, and preferably, from about 0.5 to about 20% by weight of the composition, based on total weight of the composition and including all ranges subsumed therein.

Thickeners may also be utilized as part of the cosmetically acceptable carrier in the compositions of the present invention. Typical thickeners include cross-linked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Tapioca starch may optionally be used. Natural gums suitable for the present invention include pectin, agar, guar, veegum (magnesium aluminum silicate), xanthan, sclerotium, carrageenan, pectin and combinations of these gums. Other thickeners suitable for use include taurate copolymers like Simulgel EG® and Aristoflex® AVC, the copolymers being identified by respective INCI nomenclature as sodium/acrylate/sodium acryoyldimethyltaurate and acryloyldimethyltaurate/vinyl pyrrolidone copolymer. Still other suitable thickeners include cetearyl alcohol as well as crylate-based polymer made commercially available by Seppic and sold under the name Simulgel INS 100. Amounts of the thickener may range from 0.0 to 5%, usually from 0.001 to 1%, optimally from 0.01 to 0.5% by weight.

Collectively, water, solvents (e.g., alcohols), esters, fatty acids, humectants and/or thickeners will constitute the cosmetically acceptable carrier in amounts from 1 to 99.9%, preferably from 80 to 99% by weight.

Surfactants may also be present in compositions of the present invention. Total concentration of the surfactant will range from about 0 to about 40%, and preferably, from about 0 to about 20%, optimally from about 0 to about 8% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isothionates, acyl glutamates, $C_8$-$C_{20}$ alkyl ether phosphates and combinations thereof.

Emulsifiers may be present in the composition of the present invention. Total concentration of the emulsifier may range from about 0.1 to about 20%, and preferably, from about 1 to about 10%, and most preferably, from about 1 to about 8% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, as well as emulsifying/thickening additives like hydroxyethylacrylate/sodium acryloyldimethyl taurates copolymer/squalane and mixtures thereof.

Emulsion stabilizers generally classified as vegetable based liquids may also be used. Preferred stabilizers are sold under the name Oilwax LC and made available commercially by B&T Company.

Perfumes may be used in the composition of this invention. Illustrative non-limiting examples of the types of perfumes that may be used include those comprising terpenes and terpene derivatives like those described in Bauer, K., et al., *Common Fragrance and Flavor Materials*, VCH Publishers (1990).

Illustrative yet non-limiting examples of the types of fragrances that may be used in this invention include myrcene, dihydromyrenol, citral, tagetone, cis-geranic acid, citronellic acid, or cis-geranic acid nitrile, mixtures thereof or the like.

Preferably, the amount of fragrance employed in the composition of this invention is in the range from about 0.0% to about 10%, more preferably, about 0.00001% to about 5 wt %, most preferably, about 0.0001% to about 2%.

Various types of optional active ingredients may be used in the compositions of the present invention. Actives are defined as skin benefit agents other than emollients and other than ingredients that merely improve the physical characteristics of the composition. Although not limited to this category, general examples include talcs and silicas, as well as alpha-hydroxy acids, beta-hydroxy acids, peroxides, zinc salts, and sunscreens.

Beta-hydroxy acids include salicylic acid, for example. Zinc pyrithione is an example of the zinc salts useful in the composition of the present invention.

Other suitable but optional actives for use herein include opacifiers like $TiO_2$ and ZnO and colorants like iron oxide red, yellow and black. Such opacifiers and colorants typically have a particle size from 50 to 1200 nm, and preferably, from 50 to 350 nm.

To enhance skin moisturization, actives classified as cationic ammonium compounds may optionally be used in the compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

When cationic ammonium compounds are used, preferred additional active for use with the same are moisturizing agents such as substituted ureas like hydroxymethyl urea, hydroxyethyl urea, hydroxypropyl urea; bis(hydroxymethyl) urea; bis(hydroxyethyl)urea; bis(hydroxypropyl)urea; N,N'-dihydroxymethyl urea; N,N'-di-hydroxyethyl urea; N,N'-dihydroxypropyl urea; N,N,N'-tri-hydroxyethyl urea; tetra (hydroxymethyl)urea; tetra(hydroxyethyl)urea; tetra (hydroxypropyl)urea; N-methyl-N'-hydroxyethyl urea; N-ethyl-N,N—N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-1-propyl or 2-hydroxy-1-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from about 0.01 to about 20%, and preferably, from about 0.5 to about 15%, and most preferably, from about 2 to about 10% based on total weight of the composition and including all ranges subsumed therein.

When cationic ammonium compound and substituted urea are used, in a most especially preferred embodiment at least from about 1 to about 15% glycerin external to the particle is used, based on total weight of the composition and including all ranges subsumed therein.

Compositions of the present invention may include vitamins as the desired active. Illustrative vitamins are Vitamin A (retinol) as well as retinol esters like retinol palmitate and retinol propionate, Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Octadecenedioic acid, azelaic acid, ubiquinone, dihydroxyacetone (DHA) and mixtures thereof may also be used as actives in the composition of this invention. Such compounds, when used, typically make up from about 0.2 to 4.5%, and preferably, from about 0.5 to 3% by weight of the composition, including all ranges subsumed therein.

Other optional actives suitable for use in this invention include retinoids, retinoic acid, retinol, retinal and retinyl esters, conjugated linoleic acid, petroselinic acid, resveratrol, resorcinols like 4-ethyl resorcinol, 4-hexyl resorcinol, 4-phenylethyl resorcinol, dimethoxytoluoyl propyl resorcinol, 4-cyclopentyl resorcinol, 4-cyclohexylresorcinol, alpha-an/or beta-hydroxyacids, petroselinic acid, conjugated linoleic acid, octadecanoic acid, phenylethyl resorcinol (Symwhite 377 from Symrise), undecylenol phenylalanine (Seppi White from Seppic) mixtures thereof or the like. Such actives, when used, collectively make up from about 0.001 to about 12% by weight of the composition.

Desquamation promoters may be present. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic and its derivatives, lactic and malic acids. Salicylic acid is representative of the beta-hydroxycarboxylic acids. Amounts of these materials when present may range from about 0.01 to about 15% by weight of the composition.

A variety of herbal extracts may optionally be included as actives in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary. Soy extracts may be used and especially when it is desirable to include retinol.

Also optionally suitable for use include materials like chelators (e.g., EDTA), $C_{8-22}$ fatty acid substituted saccharides, lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Occlusives like Oilwax LC or sunflower seed oil are often desired. Amounts of these materials may range from about 0.000001 to about 10%, preferably from about 0.0001 to about 1% by weight of the composition.

Sunscreen actives may also be included in compositions of the present invention. Particularly preferred are such materials as phenylbenzimidazole sulfonic acid (Ensulizole), ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide, zinc oxide, polyethylene and various other polymers. Also suitable for use is octocrylene. Amounts of the sunscreen agents when present may generally range from 0.1 to 30%, preferably from 0.5 to 20%, optimally from 0.75 to 10% by weight.

Conventional buffers/pH modifiers may be used. These include commonly employed additives like sodium hydroxide, potassium hydroxide, hydrochloric acid, citric acid and citrate/citric acid buffers. In an especially preferred embodiment, the pH of the composition of this invention is from about 4 to about 8, and preferably, from about 4.25 to about 7.75, and most preferably, from about 6 to about 7.5, including all ranges subsumed therein. The composition of this invention may be a solid stick or bar. Viscosity of the composition of this invention is, however, preferably from about 1,000 to about 120,000 cps, and most preferably, from about 5,000 to 80,000 cps, taken at ambient temperature and a shear rate of 1 $s^{-1}$ with a strain controlled parallel plate rheometer made commercially available from suppliers like T.A. Instruments under the Ares name.

Many compositions, especially those containing water, should be protected against the growth of potentially harmful microorganisms. Anti-microbial compounds, such as triclosan, and preservatives are, therefore, typically necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, methylisothiazolinone (Neolone™ 950) and ethylhexylglycerin (Sensiva®SC 50). Preservatives will usually be employed in amounts ranging from about 0.1% to 2% by weight of the composition.

When making the composition of the present invention, the desired ingredients are mixed in no particular order and usually at temperatures from about 25 to about 80° C. and under atmospheric pressure.

A wide variety of packaging can be employed to store and deliver the composition of this invention. Packaging is often dependent upon the type of personal care end-use. For instance, leave-on skin lotions and creams, and shampoos generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film. Patches, bottles, tubes, roll-ball applicators, squeeze containers or lidded jars are sometimes preferred.

The examples which follow are provided to illustrate and facilitate an understanding of the invention. The examples are not intended to limit the scope of the claims.

Example 1

| Ingredients<br>Ingredient | Sample 1<br>% W/W | Sample 2<br>% W/W | Sample 3<br>% W/W | Sample 4<br>% W/W |
|---|---|---|---|---|
| Deionized water | Balance | Balance | Balance | Balance |
| Stearic acid | 3.5 | 3.5 | 3.5 | 3.5 |
| Glyceryl stearate | 0.7 | 0.7 | 0.7 | 0.7 |
| Sunflower seed oil | 1.0 | 1 0 | 1.0 | 1.0 |
| Cetearyl alcohol | 0.5 | 0.5 | 0.5 | 0.5 |
| Carbopol | 0.14 | 0.14 | 0.14 | 0.14 |
| Magnesium aluminum silicate | 0.3 | 0.3 | 0.3 | 0.3 |
| Glycerin | 7.0 | 7.0 | 7.0 | 7.0 |
| Stearyl heptanoate & stearyl caprylate (50/50) | | | 2.4 | 2.4 |
| Dimethicone | | 1.2 | | |
| Phenoxyethanol | | | 0.7 | |
| Benzyl alcohol | | | 0.5 | |
| Ethanol | | | | 1.2 |
| Tocopherol | 0.1 | 0.1 | 0.1 | 0.1 |
| Disodium EDTA | 0.1 | 0.1 | 0.1 | 0.1 |
| Potassium hydroxide (45% Soln) | 0.5 | 0.5 | 0.5 | 0.5 |
| Preservative | 0.55 | 0.55 | 0.55 | 0.55 |
| Fragrance | 0.25 | 0.25 | 0.25 | 0.25 |

| Ingredients<br>Ingredient | Sample 5<br>% W/W | Sample 6<br>% W/W | Sample 7<br>% W/W | Sample 8<br>% W/W |
|---|---|---|---|---|
| Deionized water | Balance | Balance | Balance | Balance |
| Stearic acid | 3.5 | 3.5 | 3.5 | 3.5 |
| Glyceryl stearate | 0.7 | 0.7 | 0.7 | 0.7 |
| Sunflower seed oil | 1.0 | 1.0 | 1.0 | 1.0 |
| Cetearyl alcohol | 0.5 | 0.5 | 0.5 | 0.5 |
| Carbopol | 0.14 | 0.14 | 0.14 | 0.14 |
| Magnesium aluminum silicate | 0.3 | 0.3 | 0.3 | 0.3 |
| Glycerin | 7.0 | 7.0 | 7.0 | 7.0 |
| Stearyl heptanoate | | | 2.4 | |
| Stearyl caprylate | | | | 2.4 |
| Myristyl myristate | | 2.4 | | |
| Isopropyl palmitate | 2.4 | | | |
| Phenoxyethanol | 0.7 | 0.7 | 0.7 | 0.7 |
| Benzyl alcohol | 0.5 | 0.5 | 0.5 | 0.5 |
| Tocopherol | 0.1 | 0.1 | 0.1 | 0.1 |
| Disodium EDTA | 0.1 | 0.1 | 0.1 | 0.1 |
| Potassium hydroxide (45% Soln) | 0.5 | 0.5 | 0.5 | 0.5 |
| Preservative | 0.55 | 0.55 | 0.55 | 0.55 |
| Fragrance | 0.25 | 0.25 | 0.25 | 0.25 |

| Ingredients<br>INCI Name | Sample 9<br>% W/W | Sample 10<br>% W/W | Sample 11<br>% W/W |
|---|---|---|---|
| Deionized water | Balance | Balance | Balance |
| Stearic acid- | 3.5 | 3.5 | 3.5 |
| Glyceryl stearate | 0.7 | 0.7 | 0.7 |
| Sunflower seed oil | 1.0 | 1.0 | 1.0 |
| Cetearyl alcohol | 0.5 | 0.5 | 0.5 |
| Carbopol | 0.14 | 0.14 | 0.14 |
| Magnesium aluminum silicate | 0.3 | 0.3 | 0.3 |
| Glycerin | 7.0 | 7.0 | 7.0 |
| Stearyl heptanoate & stearyl caprylate (50/50) | 2.4 | 2.4 | 2.4 |
| Phenoxyethanol | | | 1.2 |
| Benzyl alcohol | | 1.2 | |
| Cetyl alcohol | 1.2 | | |
| Tocopherol | 0.1 | 0.1 | 0.1 |
| Disodium EDTA | 0.1 | 0.1 | 0.1 |
| Potassium hydroxide (45%) | 0.5 | 0.5 | 0.5 |
| Preservative | 0.55 | 0.55 | 0.55 |
| Fragrance | 0.25 | 0.25 | 0.25 |

The samples above were made by combining the ingredients and mixing the same with moderate shear under conditions of atmospheric pressure and temperature at about 25° C. Mixing continued until a homogeneous composition (oil-in-water emulsion) was obtained.

Example 2

The samples prepared in Example 1 above were assessed for sensory characteristics, as well as foaming and whitening upon application.

For sensory assessment, commercially available skin replacement liners (about 11.5 cm×7 cm×0.16 cm) were evenly coated with about 260 mg of composition represented as Samples 1-11. Sample was spread with a laboratory spatula and was allowed to dry at for about one (1) hour at room temperature. Subsequent to drying, a CETR Tribometer (V. 2.15, Build 90) was used (method Fri-20 g-5 mm-1 s) to assess friction over the surface of the dry composition coating. The instrument probe was placed (about 1.3 cm) over the film and the instrument was employed to measure frictional force. Three (3) runs were performed and the average frictional force was recorded in grams.

For assessment of foaming and whitening, forearms of participants were placed (palm upward) on a photography table and under the lens (about 70 cm distance) of a Canon EOS 50 D, Digital SLR camera. Photographs of participant forearms were taken prior to the use of samples in order to establish a baseline measurement. The area of capture on the forearm was about 250 cm². Standard humidity and room temperature were the conditions.

To the participant forearms, about 0.25 ml of sample was applied, the same was applied using two fingers and 5 stroke/5 second intervals. Application of the sample was carried out for a total of 5 cycles to simulate normal topical applications. Subsequent to composition application, a second photograph was taken of the forearm so that the same could be compared to baseline measurement results taken from the same participant. Image analysis was assed with Perkin Elmer Software—D65 lighting in the RGB color space. The image analysis program was run to measure and assess L, a, b values at baseline and at each 5 stroke interval. Intensity (L*) as whiteness is reported at 25 rubs or strokes.

The table below presents the sensory, whitening and sensory-foam factor results obtained in this experiment.

| Sample | Sensory Force grams | Whitening Intensity (L*) at 25 rubs | Sensory-foam factor (gL*) |
|--------|---------------------|-------------------------------------|---------------------------|
| 1      | 5.6                 | 6.1                                 | 34.2                      |
| 2      | 4.2                 | 3.6                                 | 15.1                      |
| 3      | 4.9                 | 4.9                                 | 24.0                      |
| 4      | 4.1                 | 6.9                                 | 28.3                      |
| 5      | 5.5                 | 7.7                                 | 42.4                      |
| 6      | 6.4                 |                                     |                           |
| 7      | 3.7                 |                                     |                           |
| 8      | 3.0                 |                                     |                           |
| 9      |                     | 8.6                                 |                           |
| 10     |                     | -2.7                                |                           |
| 11     |                     | 2.3                                 |                           |

The results above, unexpectedly confirm that when topical composition is made consistent with this invention (i.e., substantially free of silicones and comprising alcohol and ester as depicted by formulae 1 and 2) excellent sensory results are achieved in the absence of foaming and whitening.

Example 3

Trained panelist applied about 0.1 mg of composition made according to this invention to about 2 cm² of skin on the forearm. At a different location on the forearm, the same amount of composition comprising about one (1) percent by weight of silicone was applied to a 2 cm² area of skin. Surprisingly, all panelists confirmed that composition made according to this invention yielded sensory and whitening/foaming characteristics consistent with those of compositions not substantially free of silicone.

What is claimed is:

1. A topical composition comprising:
   a) from about 0.02 to about 5% by weight of the composition of an alcohol having the formula:

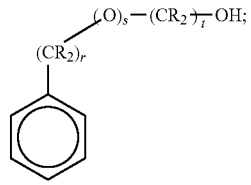

and b) from about 0.1 to 15% by weight of the composition of an ester having the formula:

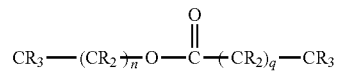

wherein each R is independently hydrogen or a methyl group;
r is 0 or 1, s is 0 or 1, t is an integer from 1 to 6, n is an integer from 5 to 20 and q is an integer from 3 to 10; wherein at least 75% of all alcohol and ester in the composition are represented by formulas I and II, respectively; and further wherein the topical composition is substantially free of silicone.

2. The topical composition according to claim 1 wherein the alcohol is one where s is zero, R is H and t is an integer from 1 to 3, R is H and t is an integer from 1 to 3, or a mixture thereof.

3. The topical composition according to claim 1 wherein the ester is one where R is H, n is 12 to 19 and q is 3 to 6.

4. The topical composition according to claim 1 wherein the alcohol is phenoxyethanol, benzylalcohol, or a mixture thereof and the ester is stearyl heptanoate, stearyl caprylate or a mixture thereof.

5. The topical composition according to claim 1 wherein the composition further comprises a sunscreen, skin whitening agent, wrinkle-reducing agent, or a mixture thereof.

6. The topical composition according to claim 1 wherein the composition is capable of imparting a soft and silky sensation free of whitening after application to skin.

7. The topical composition according to claim 1 wherein the composition is a leave-on composition.

8. A method for imparting a silky feeling to skin by applying to skin the composition according to claim 1.

9. The composition according to claim 1 wherein the composition yields a sensory-foam factor of 25 gL*.

* * * * *